United States Patent [19]

Deford et al.

[11] Patent Number: 5,198,445
[45] Date of Patent: Mar. 30, 1993

[54] COMPOSITION AND USE OF SUBSTITUTED 3-THIO-2-PROPYNENITRILES AS INDUSTRIAL ANTIMICROBIALS

[75] Inventors: Connie L. Deford; Charles D. Gartner; Kalakota S. Reddy, all of Midland, Mich.; John K. Swayze, Carmel, Ind.; David E. Wallick, Midland, Mich.; Warren L. Treptow, Midland, Mich.; George A. Paul, Midland, Mich.; Billy R. Hardas, Midland, Mich.

[73] Assignee: The Dow Chemical Company, Midland, Mich.

[21] Appl. No.: 871,260

[22] Filed: Apr. 20, 1992

Related U.S. Application Data

[63] Continuation-in-part of Ser. No. 633,866, Dec. 26, 1990, Pat. No. 5,126,349, which is a continuation-in-part of Ser. No. 464,085, Jan. 12, 1990, abandoned.

[51] Int. Cl.$^5$ ................. A61K 275/00; A61K 31/395
[52] U.S. Cl. .................................... 514/269; 514/274; 514/361; 514/369; 514/519; 514/520; 514/526
[58] Field of Search ............... 514/269, 274, 361, 369, 514/519, 520, 526

[56] References Cited

U.S. PATENT DOCUMENTS

| | | | |
|---|---|---|---|
| 3,140,306 | 7/1964 | Heininger | 260/465 |
| 4,172,892 | 10/1979 | Nannini et al. | 424/246 |
| 4,238,405 | 12/1980 | Felix | 268/464 |
| 4,388,314 | 6/1983 | Nannini et al. | 424/246 |
| 4,529,721 | 7/1985 | Nagata et al. | 514/191 |
| 5,039,702 | 8/1991 | Brandman et al. | 514/526 |

FOREIGN PATENT DOCUMENTS 0104432 8/1983 European Pat. Off. .
89/07890 8/1989 World Int. Prop. O. .

Primary Examiner—Johann Richter

[57] ABSTRACT

Substituted 3-thio-2-propynenitriles are prepared which correspond to the formula:

$$R-S-C\equiv C-C\equiv N$$

wherein R is an alkyl, cyclic alkyl, aryl, or heterocyclo group.

These compounds have been found to exhibit a high degree of antimicrobial activity in industrial and commercial applications and compositions containing these compounds are so employed.

18 Claims, No Drawings

COMPOSITION AND USE OF SUBSTITUTED 3-THIO-2-PROPYNENITRILES AS INDUSTRIAL ANTIMICROBIALS

CROSS-REFERENCE TO RELATED APPLICATION

This is a continuation-in-part of copending U.S. application Ser. No. 07/633,866, filed Dec. 26, 1990 now U.S. Pat. No. 5,126,349, which is a continuation-in-part of U.S. application Ser. No. 07/464,085, filed Jan. 12, 1990, now abandoned.

BACKGROUND OF THE INVENTION

The desirability of identifying or discovering new antimicrobial agents is widely recognized. New antimicrobial agents are desired for several reasons; these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

U.S. Pat. Nos. 4,172,892 and 4,388,314 disclose a large number of acids, one of which has the formula:

which is used as a reactant in a process to produce a compound of the formula:

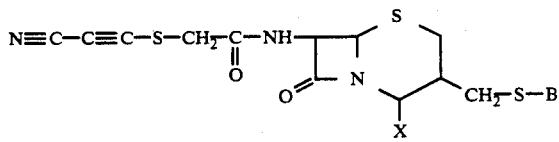

wherein X is a free or esterified carboxy group and B is a substituted tetrazolyl or thiadiazolyl radical or a heterobicyclic ring. This compound is taught to be useful in pharmaceutical and veterinary compositions, as well as antibacterial activities. This reference, however, provides no teaching that the acid of the formula:

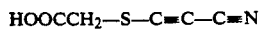

is itself useful as an antimicrobial agent.

U.S. Pat. No. 5,039,702 discloses an α-halo-β-(substituted)thio-acrylonitrile of the formula:

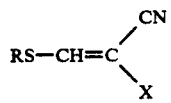

wherein X is a halogen and R is a lower alkyl, aryl, aralkyl, heterocyclo, or a thiocarbonyl group. This compound is taught to be useful as an effective antimicrobial agent.

This reference does not, however, provide any teaching that the α-halo-β-(substituted)thioacrylonitrile may be further reacted to prepare the substituted 3-thio-2-propynenitriles of the present invention, or that such substituted 3-thio-2-propynenitriles would be effective antimicrobial agents.

SUMMARY OF THE INVENTION

The present invention is directed to substituted 3-thio-2-propynenitriles, a method of making such substituted 3-thio-2-propynenitriles, and compositions containing said compounds and the use of such compositions as anitmicrobials in industrial or commerical uses. The compounds of the present invention correspond to the formula:

wherein R is an alkyl, cyclic alkyl, aryl, or heterocyclo group.

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a method for inhibiting microorganisms, particularly bacteria, fungi, and algae which comprises contacting said microorganisms or habitat thereof with an effective amount of the compound of this invention.

The antimicrobial compounds of this invention may be added directly to aqueous formulations susceptible to microbial growth, either undiluted or dissolved in organic solvents like glycols, alcohols, acetone and the like. They may also be added alone or in combination with other preservatives.

DETAILED DESCRIPTION OF THE INVENTION

In the present specification and claims, the term "alkyl" is employed to designate straight chain and branched chain alkyls. Such alkyls may be with or without substituents, such as cyclic alkyl, aryl, alkoxy or halogen. Preferably, the term "alkyl" is employed to designate straight chain alkyls of 1 to 18 carbon atoms and branched chain alkyls of 3 to 18 carbon atoms. Most preferably, the term "alkyl" is employed to designate straight chain alkyls of 1 to 12 carbon atoms, such as methyl, ethyl, propyl, butyl, decyl, or dodecyl and branched chain alkyls of 3 to 12 carbon atoms, such as isopropyl or tertiary butyl.

In the present specification and claims, the term "cyclic alkyl" is employed to designate a closed-ring alkyl structure. Such cyclic alkyls may be with or without substituents, such as alkyl, aryl, alkoxy or halogen. Preferably, the term "cyclic alkyl" is employed to designate cyclic alkyls of 3 to 8 carbon atoms. Most preferably, the term "cyclic alkyl" is employed to designate cyclic alkyls of 3 to 6 carbon atoms, such as cyclopentyl or cyclohexyl.

In the present specification and claims, the term "aryl" is employed to designate groups which have the ring structure characteristic of benzene, wherein the ring may be with or without substituents such as alkyl, cyclic alkyl, alkoxy, or halogen. The aryl ring may also be a fused ring, wherein the ring may have one or more of its sides in common with another ring. Preferably, the aryl ring has no more than three substituents. Most preferably, the aryl is phenyl, naphthyl, or chlorophenyl.

In the present specification and claims, the term "heterocyclo" is employed to designate a closed-ring structure containing at least one ring carbon, in which one or more of the atoms in the ring is an element other than carbon. Such heterocyclos may be with or without substituents, such as alkyl, cyclic alkyl, aryl, alkoxy, or halogen. The heterocyclo ring may also be a fused ring, wherein the ring may have one or more of its sides in common with another ring. Preferably, the closed-ring structure will consist of 5 or 6 atoms. Preferably, the non-carbon ring atom or atoms will be nitrogen, oxygen or sulfur. Preferably, the ring has no more than three substituents. Most preferably, the heterocyclo is thiazolyl, triazolyl, imidazolyl, or pyrimidyl.

As used herein, the term "microorganism" is meant to refer to bacteria, fungi, viruses, algae, subviral agents and protozoa.

As used herein, the term "effective amount" refers to that amount of one or a mixture of two or more of the compounds of this invention needed to exhibit inhibition of selected organisms. Typically, this amount varies from about 1 part per million (ppm) to about 5,000 ppm by weight of the compound or compounds in a microbial habitat being contacted with the compound. Such amounts vary depending upon the particular compound tested and organism treated and the conditions under which such microorganism or microbial habitat is treated. Also, the exact concentration of the compounds to be added in the treatment of industrial and consumer formulations may vary within a product type depending upon the components of the formulation. In such formulations, the compounds of this invention may be added as a liquid concentrate or diluted with additional liquid to produce the ultimate treating composition, wherein the liquid could be water or an organic solvent like glycols, alcohols, acetone and the like. A preferred antimicrobially effective amount of the compound or a mixture of compounds is from about 1 ppm to about 500 ppm, more preferably from about 1 ppm to about 50 ppm by weight, in a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system or a formulated product such as a styrene-butadiene latex, a tape joint, a hand lotion, or a shampoo.

The terms "inhibition", "inhibit" or "inhibiting" refer to suppression, control, stasis, kill or any other interference with the normal life processes of microorganisms that is adverse to such microorganisms.

The compounds of the present invention can be prepared by the reaction of an appropriate-substituted 2-chloro-3-thio-2-propenenitrile precursor with basic aqueous solution (such as sodium hydroxide solution). In carrying out this reaction, the appropriately-substituted 2-chloro-3-thio-2-propenenitrile precursor and the basic aqueous solution are mixed together in substantially equimolar amounts. The general reaction scheme is as follows:

A preferred method of preparing the compounds of the present invention is to carry out the dehydrochlorination of the appropriately-substituted 2-chloro-3-thio-2-propenenitrile precursor at a temperature below ambient, in the presence of water and an inert, water-miscible solvent such as tetrahydrofuran, dioxane, isopropanol, polyglycols and their ethers, dimethylformamide, and the like, with the subsequent addition of a known Lewis base such as an alkaline earth metal hydroxide. As used herein, "Lewis base" refers to compounds that form a covalent bond by donating a pair of electrons, with neutralization resulting from a reaction between the base and an acid with formation of a covalent bond.

The reaction rate of this preferred method of preparing the compounds of the present invention is conveniently controlled by the rate of base addition coupled with external cooling. Room temperature, however, may be used as the starting reaction temperature to increase the reaction rate. The reaction may also be accelerated by increasing the amount of inert, water-miscible solvent. An increase in the amount of inert, water-miscible solvent also makes the reaction mixture more homogeneous.

Advantages of using this preferred method of preparing the compounds of the present invention include mild reaction conditions, a high yield reaction, relatively inexpensive reagents, and a short reaction time. In addition, by using an inert, water-miscible solvent, a solvent extraction step can be eliminated because a desired product may be directly formulated as compared to a reaction process that uses a water-immiscible solvent to isolate the desired product. The reaction yield of this preferred method is also sufficiently high such that purification of a desired final product may not be required.

Tetraethylene glycol, for example, is a common formulating solvent for paints, pigment slurries, latexes, and metal working fluids. By using tetraethylene glycol as the inert, water-miscible solvent in the dehydrochlorination reaction, a desired composition may be directly formulated which could be used directly into a paint, pigment slurry, latex, or metal working fluid product.

SYNTHESIS OF INTERMEDIATE APPROPRIATELY-SUBSTITUTED 2-CHLORO-3-THIO-2-PROPENENITRILE

The synthesis of the appropriately-substituted 2-chloro-3-thio-2-propenenitrile precursor begins with the chlorination of acrylonitrile to form 2,2,3-trichloropropionitrile. This chlorination is straightforward and is described in the art, such as in N. C. Lorette, "The Addition of Chlorine to Acrylonitrile", *J. Org. Chem.*, Vol. 26, pp. 2324–2327, 1960. Overall yields of over 90 percent based on acrylonitrile are achievable.

Dehydrochlorination of 2,2,3-trichloropropionitrile yields an isomeric mixture of 2,3-dichloroacrylonitrile. This dehydrochlorination can be carried out by heating the 2,2,3-trichloropropionitrile in the presence of a catalyst with yields of 80 to 100 percent. Known catalysts include, but are not limited to, organic bases such as pyridine, polyvinylpyridine, and their hydrochloride salts and phase transfer catalysts such as tetraphenylphosphonium chloride, tetrabutylammonium chloride and ion exchange resins. Purification of the 2,3-dichloroacrylonitrile prior to subsequent reaction is optional.

The 2,3-dichloroacrylonitrile reacts with an alkaline earth metal salt of an appropriate mercaptan to form the appropriately-substituted 2-chloro-3-thio-2-propenenitrile precursor in alkanols or aprotic solvents. The reaction temperature, stoichiometries, and mode of addition are important to obtain acceptable isolated yields (greater than 85 percent from 2,3-dichloroacrylonitrile).

The following examples illustrate the present invention and the manner by which it can be practiced but, as such, should not be construed as limitations upon the overall scope of the same.

EXAMPLE 1

Preparation of 3-Methylthio-2-Propynenitrile

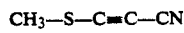

Water (95 ml) is added to a 250 ml roundbottom flask equipped with an addition funnel, condenser, thermometer, pH probe and magnetic stirring bar. 2-Chloro-3-methylthio-2-propenenitrile (2.64 g, 97 percent purity) is then added. The head space of the reactor is padded with nitrogen.

An aqueous NaOH solution is produced by mixing 1N NaOH (22.5 ml) with water (40 ml). This NaOH solution is added to the addition funnel.

The aqueous NaOH solution is added to the flask over a 20-hour period while maintaining the solution at room temperature or below. A temperature between zero and 5° C. is preferred.

The reaction mixture is cooled to 5° C. Dichloromethane (30 ml) is added to the reaction mixture. The two-phase system is agitated and then transferred to a separatory funnel. The dichloromethane phase is removed and the dichloromethane is vacuum distilled off. The remaining material weighs 1.70 g. Gas chromatographic analysis (GC) of the residue reveals 71 percent by area 3-methylthio-2-propynenitrile. A calculated overall yield of 64 percent is achieved.

The crude reaction product is purified by column chromatography yielding 3-methylthio-2-propynenitrile in greater than 99 percent purity (by GC). The structure identity is confirmed by proton ($^1$H) and carbon nuclear magnetic resonance spectroscopy (NMR), infrared spectroscopy (IR) and gas chromatography/mass spectrometry (GC/MS).

EXAMPLE 1A

Preparation of 3-Methylthio-2-Propynenitrile Using a Preferred Reaction Procedure Into a 1,000 ml reaction flask is charged 2-chloro-3-methylthio-2-propenenitrile (150.4 g; 1.12 moles), tetrahydrofuran (230 ml) and water (180 ml) and then 4N aqueous sodium hydroxide solution (267 ml, 1.06 moles) is slowly added in at zero degree Celsius with stirring at such a rate so as to maintain the reaction pH below 11. The mixture becomes dark brown. Progress of the reaction is monitored by GC. The resultant mixture is stirred at room temperature for 8 hours and then diluted with 150 ml of saturated aqueous sodium chloride solution. The product is extracted twice with 150 ml portions of dichloromethane. The dichloromethane extract is dried over anhydrous sodium sulfate, filtered and concentrated on a rotary evaporator to yield 106.8 g of dark brown oil. The dark brown oil is purified by fractional distillation to give 88 g of 3-methylthio-2-propynenitrile as a colorless clear oil (yield, 81 percent) which is greater than 99.5 percent pure by GC. It is further characterized by GC/MS, IR and $^1$H NMR.

EXAMPLE 2

Preparation of 3-Ethylthio-2-Propynenitrile

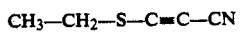

Into a 250 ml reaction flask is charged 2-chloro-3-ethylthio-2-propenenitrile (8.2 g; 0.055 moles), tetrahydrofuran (15 ml) and water (50 ml) and then 1N aqueous sodium hydroxide solution (55.6 ml, 0.055 moles) is slowly added in at zero degree Celsius with stirring at such a rate so as to maintain the reaction pH below 11. The mixture becomes dark brown. Progress of the reaction is monitored by GC. The resultant mixture is stirred at room temperature for 8 hours and then diluted with 150 ml of saturated aqueous sodium chloride solution. The product is extracted twice with 100 ml portions of dichloromethane. The dichloromethane extract is dried over anhydrous sodium sulfate, filtered and concentrated on a rotary evaporator to yield 6.8 g of dark brown oil. The dark brown oil is purified by silica gel flash column chromatography to give 4.0 g of 3-ethylthio-2-propenenitrile as a colorless clear oil (yield, 66 percent) which is greater than 99 percent pure by GC. It is further characterized by GC/MS, IR and $^1$H NMR.

EXAMPLE 3

Preparation of 3-t-Butylthio-2-Propynenitrile

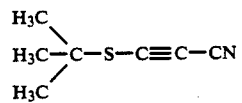

Into a 250 ml reaction flask is added 2-chloro-3-t-butylthio-2-propenenitrile (1.8 g, 0.01 moles), tetrahydrofuran (35 ml), and water (35 ml). The mixture is stirred at zero degree Celsius until the solid is completely dissolved and then aqueous sodium hydroxide solution (10 ml 1N NaOH, 0.010 moles, diluted with 50 ml water) is added slowly with stirring at such a rate so as to maintain the reaction pH below 11. The progress of the reaction is monitored by GC. The resultant reaction mixture is stirred at zero degree Celsius for three hours followed by one hour at room temperature and then diluted with 50 ml of saturated NaCl solution. The product is extracted twice with 100 ml portions of dichloromethane. The combined dichloromethane extract is dried over anhydrous sodium sulfate, filtered and the filtrate is evaporated under vacuum to give 1.5 g of colorless oil. This oil is purified by silica gel column chromatography to yield 0.86 g 3-t-butylthio-2-propynenitrile (yield 61 percent), which is greater than 99 percent pure by GC. It is further characterized by GC/MS and IR.

EXAMPLE 4

Preparation of 3-Cyclopentylthio-2-Propynenitrile

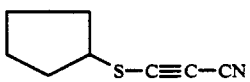

Into a 250 ml reaction flask is added 2-chloro-3-cyclopentylthio-2-propenenitrile (4.0 g, 0.026 moles), tetrahydrofuran (40 ml) and water (40 ml) and then aqueous sodium hydroxide solution (27 ml 1N NaOH, 0.027 moles, diluted with 80 ml water) is added at zero degree Celsius slowly with stirring at such a rate so as to maintain the reaction pH below 11. The progress of the reaction is monitored by GC. The resulting mixture is stirred at room temperature for 4 hours and then diluted with 100 ml of saturated aqueous NaCl solution. The product is extracted twice with 100 ml portions of dichloromethane. The combined dichloromethane extract is dried over anhydrous sodium sulfate, filtered and the filtrate is concentrated under vacuum to give 4.0 g of brown oil. This oil is purified by silica gel column chromatography to yield 2.2 g of 3-cyclopentylthio-2-propynenitrile (yield 69 percent) which is greater than 99 percent pure by GC. It is characterized by GC/MS, IR and $^1$H NMR.

EXAMPLE 5

Preparation of 3-(4-Chlorophenyl)Thio-2-Propynenitrile

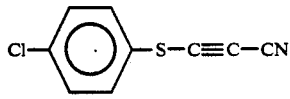

Into a 250 ml reaction flask is added 2-chloro-3-(4-chlorophenyl)thio-2-propenenitrile (4.0 g, 0.017 moles), tetrahydrofuran (40 ml) and water (40 ml). The mixture is stirred at zero degree Celsius until the solid is completely dissolved and then an aqueous sodium hydroxide solution (45 ml, 0.016 moles) is added slowly with stirring at such a rate so as to maintain the reaction pH below 11. The progress of the reaction is monitored by GC. The resultant reaction mixture is stirred at zero degree Celsius for 30 minutes and then diluted with 100 ml of saturated aqueous NaCl solution. The product is extracted twice with 100 ml portions of dichloromethane. The combined dichloromethane extract is dried over anhydrous sodium sulfate, filtered and the filtrate is evaporated under vacuum to give 2.9 g of white solid. This solid is purified by silica gel column chromatography to yield 0.8 g 3-(4-chlorophenyl)-thio-2-propynenitrile as colorless shiny flakes (yield 25 percent), which is greater than 99 percent pure by GC. It is further characterized by GC/MS and IR.

EXAMPLE 6

Preparation of 3-(2-Pyrimidyl)Thio-2-Propynenitrile

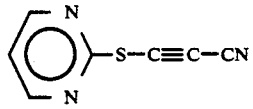

Into a 250 ml reaction flask is added 2-chloro-3-(2-pyrimidyl)thio-2-propenenitrile (1.5 g, 0.007 moles), tetrahydrofuran (35 ml) and water (35 ml). The mixture is stirred at zero degree Celsius until the solid is completely dissolved and then aqueous sodium hydroxide solution (7.5 ml 1N NaOH, 0.0075 moles, diluted with 50 ml water) is added slowly with stirring at such a rate so as to maintain the reaction pH below 11. The resultant reddish brown solution is stirred at zero degree Celsius for three hours followed by one hour at room temperature and then diluted with 50 ml of saturated aqueous NaCl solution. The product is extracted twice with 100 ml portions of dichloromethane. The combined dichloromethane extract is dried over anhydrous sodium sulfate, filtered and the filtrate is evaporated under vacuum to give 0.5 g of pale yellow solid (yield 40 percent, purity 90 percent by GC/MS) which is characterized by GC/MS and $^1$H NMR.

EXAMPLE 7

Preparation of 3-Decylthio-2-Propynenitrile

Into a 50 ml reaction flask is charged 2-chloro-3-decylthio-2-propenenitrile (1.0 g, 0.0038 moles) and 50 ml of water. The mixture is stirred at room temperature for 10 minutes and then 0.5N aqueous sodium hydroxide (7.70 ml) solution is added slowly. The resultant mixture is heated to 80° C. and held at that temperature for 16 hours. The mixture is then cooled to room temperature and the product is recovered by extraction using two 50 ml portions of dichloromethane. The combined dichloromethane extracts are dried over anhydrous Na$_2$SO$_4$, filtered and concentrated on a rotary evaporator to yield 0.66 g of brown oil. This oil is purified by silica gel column chromatography to give 0.25 g of 3-decylthio-2-propynenitrile (yield 29 percent) which is 80 percent pure by GC/MS.

EXAMPLE 8

Preparation of 3-Dodecylthio-2-Propynenitrile

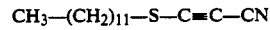

Into a 50 ml reaction flask is charged 2-chloro-3-dodecylthio-2-propenenitrile (1.7 g, 0.0059 moles), 30 ml of dichloromethane and 50 ml of water. The mixture is stirred at room temperature for 10 minutes and then 0.5N aqueous sodium hydroxide (7.7 ml, 0.0039 moles) solution is added slowly. The resultant mixture is stirred for 12 hours. The product is extracted twice with 50 ml portions of dichloromethane. The combined dichloromethane extract is dried over anhydrous Na$_2$SO$_4$, filtered and concentrated on a rotary evaporator to yield 2.0 g of brown oil. This oil is purified by silica gel column chromatography to give 0.78 g of 3-dodecylthio-2-propynenitrile (yield 53 percent) which is 80 percent pure by GC/MS.

ANTIMICROBIAL ACTIVITY

The compounds of the present invention are useful because of their antimicrobial activity and can be used as antibacterial and/or antifungal agents. Their effectiveness varies with the concentration of the compound used and the particular organisms to be controlled. While not all compounds are effective at the same concentrations, all the compounds of the present invention are useful as antimicrobial agents in the methods described herein.

TABLE I
Identification of Compounds used in Antimicrobial Activity Tests

| Compound No. | Chemical Identity |
|---|---|
| A | 3-methylthio-2-propynenitrile |
| B | 3-ethylthio-2-propynenitrile |
| C | 3-cyclopentylthio-2-propynenitrile |
| D | 3-(4-chlorophenylthio)-2-propynenitrile |
| E | 3-decylthio-2-propynenitrile |
| F | 3-dodecylthio-2-propynenitrile |

The antimicrobial activity of the compounds of the present invention is demonstrated by the following techniques.

The minimum inhibitory concentration (MIC) for the compounds listed in Table I is determined for 9 bacteria, using nutrient agar, and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol (TRITON ® X-100, a trademark of Rohm & Haas Company) to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II
Organisms used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds described in Table I as compared to the MIC of a standard commercial preservative (DOWICIL ® 75, a trademark of The Dow Chemical Company, with 1-(3-chloroally)-3,5,7-triaza-1-azoniaadamantane chloride as the active agent) are set forth for the nine bacteria organisms and six yeast/fungi organisms which are listed in Table II.

TABLE III
Minimum Inhibitory Concentrations for Test Compounds in Bacteria Species (in ppm)

| Compound | ORGANISMS | | | | | | | | |
|---|---|---|---|---|---|---|---|---|---|
| | Bs | Ea | Ec | Kp | Pv | PRD | Pa | Sc | Sa |
| DOWICIL ® 75 | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |

TABLE III-continued

Minimum Inhibitory Concentrations for Test Compounds in Bacteria Species (in ppm)

| Compound | | Bs | Ea | Ec | Kp | Pv | PRD | Pa | Sc | Sa |
|---|---|---|---|---|---|---|---|---|---|---|
| (A) | pH 6.8 | 2.5 | 2.5 | 2.5 | 2.5 | <1.0 | 2.5 | 2.5 | 2.5 | 2.5 |
|     | pH 8.2 | 5.0 | 25 | 5.0 | 10 | 2.5 | 5.0 | 2.5 | 5.0 | 5.0 |
| (B) | pH 6.8 | 25 | 25 | 5.0 | 5.0 | <1.0 | 25 | 25 | 5.0 | 5.0 |
|     | pH 8.2 | 25 | 25 | 10 | 5.0 | 5.0 | 25 | 25 | 10 | 10 |
| (C) | pH 6.8 | 100 | 100 | <10 | <10 | <10 | 250 | 250 | <10 | <10 |
|     | pH 8.2 | 250 | 100 | <10 | 25 | <10 | 250 | 250 | 25 | <10 |
| (D) | pH 6.8 | <10 | <10 | <10 | <10 | <10 | 25 | 25 | <10 | <10 |
|     | pH 8.2 | 50 | 50 | 50 | 50 | 50 | 100 | 100 | 50 | 25 |
| (E) | pH 6.8 | 100 | >500 | >500 | >500 | >500 | >500 | >500 | >500 | 25 |
|     | pH 8.2 | 25 | >500 | 100 | >500 | >500 | 25 | 500 | >500 | 25 |
| (F) | pH 6.8 | 100 | >500 | >500 | >500 | >500 | >500 | >500 | >500 | >500 |
|     | pH 8.2 | 100 | >500 | >500 | >500 | >500 | 100 | 500 | >500 | 25 |

TABLE IV

Minimum Inhibitory Concentrations for Test Compounds in Yeast/Fungi Species (in ppm)

| COMPOUND | An | Ca | Pc | Sc | Tv | Ap | Fo |
|---|---|---|---|---|---|---|---|
| DOWICIL ® 75 | >500 | >500 | >500 | 500 | >500 | >500 | >500 |
| A | 2.5 | 0.50 | 0.25 | 0.50 | 0.25 | 2.5 | 0.50 |
| B | 2.5 | <1.0 | <1.0 | <1.0 | 10 | <1.0 | <1.0 |
| C | 2.5 | 2.5 | <1.0 | 2.5 | 2.5 | 2.5 | <1.0 |
| D | <1.0 | <1.0 | <1.0 | <1.0 | 2.5 | <1.0 | <1.0 |
| E | >500 | >500 | 500 | 25 | 500 | >500 | 500 |
| F | >500 | >500 | 500 | >500 | >500 | >500 | >500 |

Additionally, the ability of the compounds of Table I to serve as preservatives in a variety of formulated industrial, household, and commercial products is tested using a Multiple Challenge Test Protocol. In this test, the formulations include a styrene-butadiene latex, a tape joint, a hand lotion, and a shampoo. The styrene-butadiene latex test formulation used is Latex DL 238A, available from The Dow Chemical Company. The compositions of the tape joint, hand lotion and shampoo test formulations can be found in Tables V-VII.

TABLE V

Tape Joint Test Formulation

| Raw Material | Percent Weight |
|---|---|
| Calcium Carbonate | 60.00 |
| Mica | 4.00 |
| Attapulgite Clay | 2.00 |
| Hydroxypropyl Methylcellulose | 0.40 |
| Polyvinyl acetate Latex | 3.00 |
| Ethylene Glycol | 0.34 |
| Water | 30.24 |
| Defoamer | 0.02 |

TABLE VI

Hand Lotion Test Formulation

| Raw Material | Percent Weight |
|---|---|
| Deionized Water | 78.60 |
| Carboxymethylcellulose | 0.15 |
| Propylene Glycol | 5.00 |
| Stearic Acid | 3.00 |
| Stearyl Alcohol | 1.00 |
| Cetyl Alcohol | 0.50 |
| Glyceryl Monostearate | 4.00 |
| Mineral Oil | 5.00 |
| Silicone | 0.50 |
| Deionized Water | 2.00 |
| Triethanolamine | 0.25 |

TABLE VII

Shampoo Test Formulation

| Raw Material | Percent Weight |
|---|---|
| Deionized Water | 60.00 |
| Sodium Lauryl Ether Sulfate | 30.00 |
| Hydrolyzed Keratin Protein | 1.00 |
| Hydrolyzed Animal Protein | 4.00 |
| Cocamide DEA | 2.00 |
| Cocamidopropyl Betaine | 1.00 |
| Sodium Chloride | 0.50 |
| Citric Acid | qs |

The formulations are separated into 50 g aliquots and placed in sterile bottles. An appropriate amount of a fresh one percent stock solution of the test compound in acetone-water is added to achieve the desired final concentrations. A small portion of each of the test formulations is streaked onto Tryptic Soy Agar (TSA) petri plates using sterile cotton swabs to ensure that the formulations are sterile. If the formulation is sterile, then it is inoculated with 0.1 ml of a mixture of equal aliquots of the 24 hour cultures of each of the bacterial organisms listed in Table II. The test formulations are then incubated at 30° C. After 24 hours, each sample is streaked onto a TSA petri plate using a sterile swab. All plates are then incubated at 30° C. for 48 hours and then rated for microbial growth using the rating system listed in Table VIII. Samples with a rating of 3 or less are reinoculated as described in the procedure for the first inoculation. Samples with a rating of 4 or greater are not reinoculated but after another 24 hours are restreaked on TSA agar.

TABLE VIII

Microbial Growth Rating System

| Rating | No. of Colonies |
|---|---|
| 1 | 0 |
| 2 | 1-4 |

TABLE VIII-continued

| Microbial Growth Rating System | |
|---|---|
| Rating | No. of Colonies |
| 3 | 5–10 |
| 4 | 11–25 |
| 5 | 26–50 |
| 6 | 51–100 |
| 7 | 101–200 |
| 8 | 201–300 |
| 9 | Too Many To Count |
| 10 | Solid Mass |

The normal interpretation of the results is that a concentration of the antimicrobial being tested is considered to be effective if no ratings greater than a 3 are observed throughout the 10 challenges. The Minimum Effective Concentration (MEC), which is used to compare the activity of the antimicrobial additives in the end-use formulations, is the minimum level that is effective under the conditions of the Multiple Challenge Test.

Under the conditions of the Multiple Challenge test, good protection is obtained in styrene-butadiene latexes used for paper coatings, inks, adhesives, soaps, cutting oils, and textiles when the compounds of the invention are added at 0.001 to 0.025 percent by weight of the formulation. An example of the effectiveness of the compounds of the invention as compared to a commercial standard in a particular styrene-butadiene latex is listed in Table IX.

TABLE IX

| MEC of Test Compounds in Styrene-Butadiene Latex Formulation (in ppm) | |
|---|---|
| Compound | MEC |
| DOWICIL ® 75 | 250 ppm |
| A | 10 ppm |
| B | 25 ppm |
| C | 100 ppm |
| D | 100 ppm |

In the preservation of latex-based paints and tape joints against the destruction caused by growth of bacteria and fungi, the compounds of the invention are added at concentrations of at least 0.002 percent by weight. This effectiveness can be compared to that of the commercial standard (DOWICIL ® 75) in a tape joint compound, under the conditions of the Multiple Challenge Test, in the results in Table X.

TABLE X

| MEC of Test Compounds in Tape Joint Formulation (in ppm) | |
|---|---|
| Compound | MEC |
| DOWICIL ® 75 | 400 ppm |
| A | 10 ppm |
| B | 25 ppm |
| C | 100 ppm |
| D | 100 ppm |

In the preservation of personal care products like hand creams, lotions, shampoos, and hand soaps, good protection is obtained at concentrations from 0.001 to 0.03 percent by weight of the formulation. The results in Tables XI and XII confirm the effectiveness of the compounds as compared to the commercial standard (DOWICIL ® 75) under the conditions of the Multiple Challenge Test.

TABLE XI

| MEC of Test Compounds in Hand Lotion Formulation (in ppm) | |
|---|---|
| Compound | MEC |
| DOWICIL ® 75 | 250 ppm |
| A | 10 ppm |
| B | 25 ppm |
| C | 250 ppm |
| D | 250 ppm |

TABLE XII

| MEC of Test Compounds in Shampoo Formulation (in ppm) | |
|---|---|
| Compound | MEC |
| DOWICIL ® 75 | 750 ppm |
| A | 10 ppm |
| B | 25 ppm |
| C | 100 ppm |
| D | 100 ppm |

MIXTURE OF A SUBSTITUTED 2-CHLORO-3-THIO-2-PROPENENITRILE AND A LIKE-SUBSTITUTED 3-THIO-2-PROPYNENITRILE

An appropriately-substituted 2-chloro-3-thio-2-propenenitrile will generally exist as a reaction product with both an E isomer and a Z isomer, as shown below, wherein R is as defined hereinabove.

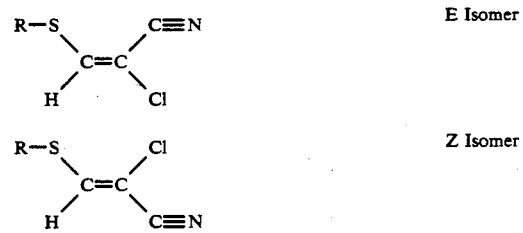

The ratio of E isomer to Z isomer of an appropriately-substituted 2-chloro-3-thio-2-propenenitrile reaction product is largely dependent on the reaction process and conditions employed to produce the appropriately-substituted 2-chloro-3-thio-2-propenenitrile. As such, an appropriately-substituted 2-chloro-3-thio-2-propenenitrile reaction product will generally exist with about 50 to 10 weight percent E isomer and about 50 to 90 weight percent Z isomer, based on a total weight of the appropriately-substituted 2-chloro-3-thio-2-propenenitrile. A typical appropriately-substituted 2-chloro-3-thio-2-propenenitrile reaction product will generally exist with about 25 weight percent E isomer and about 75 weight percent Z isomer.

It has also been discovered that the Z isomer of an appropriately-substituted 2-chloro-3-thio-2-propenenitrile precursor may degrade in situ to a like-substituted 3-thio-2-propynenitrile. The half-life for the degradation of the Z isomer of 2-chloro-3-methylthio-2-propenenitrile to 3-methylthio-2-propynenitrile has been found, for example, to be approximately two days at pH 9 and approximately two months at pH 7.

The pure E and the pure Z isomers of 2-chloro-3-methylthio-2-propenenitrile are isolated by flash column chromatography and tested for antimicrobial activity. Table XIII identifies the compounds or mixtures of compounds used in the following antimicrobial activity tests. The ratio mixtures for Compounds G, J, K, and L are based upon weight percent.

TABLE XIII

Identification of Compounds used in Anitmicrobial Activity Tests

| Compound No. | Chemical Identity |
|---|---|
| A | 3-(methylthio)-2-propynenitrile |
| G | 2-chloro-3-(methylthio)-2-propenenitrile (approximately 25:75 ratio mixture of E isomer to Z isomer) |
| H | E isomer of 2-chloro-3-(methylthio)-2-propenenitrile |
| I | Z isomer of 2-chloro-3-(methylthio)-2-propenenitrile |
| J | 90:10 ratio mixture of Compound G to A |
| K | 80:20 ratio mixture of Compound G to A |
| L | 50:50 ratio mixture of Compound G to A |

The following MIC and MEC antimicrobial tests, whose results are shown in Tables XIII–XVII, are performed using the same methods as described hereinabove.

As can be seen in Table XIV, the Z isomer of 2-chloro-3-methylthio-2-propenenitrile (Compound I) has antimicrobial activity which is essentially equivalent to 3-methylthio-2-propynenitrile (Compound A) and 25–50 times greater than the E isomer of 2-chloro-3-methylthio-2-propenenitrile (Compound H) at a pH of 8.2, due to the partial conversion of the Z isomer to 3-methylthio-2-propynenitrile.

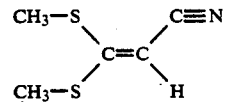

Antimicrobial compositions containing both an appropriately-substituted 2-chloro-3-thio-2-propenenitrile precursor and a like-substituted 3-thio-2-propynenitrile are formulated. Such antimicrobial compositions generally exhibit an increased potency of antimicrobial activity as compared to the appropriately-substituted 2-chloro-3-thio-2-propenenitrile precursor alone and also result in a more stable level of the like-substituted 3-thio-2-propynenitrile than the like-substituted 3-thio-2-propynenitrile alone, thus generally resulting in greater antimicrobial activity over an extended time period.

Such an antimicrobial composition containing both an appropriately-substituted 2-chloro-3-thio-2-propeneitrile precursor and a like-substituted 3-thio-2-propynenitrile will contain between about 50 to about 95 weight percent, preferably between about 80 to about 90 weight percent, of the appropriately-substituted 2-chloro-3-thio-2-propenenitrile precursor and between about 50 to about 5 weight percent, preferably between about 20 to about 10 weight percent, of the like-substituted 3-thio-2-propynenitrile, based on a total

TABLE XIV

Minimum Inhibitory Concentrations for Test Compounds in Bacteria Species (in ppm)

| Compound | | Bs | Ea | Ec | Kp | Pv | PRD | Pa | Sc | Sa |
|---|---|---|---|---|---|---|---|---|---|---|
| (A) | pH 6.8 | 2.5 | 2.5 | 2.5 | 2.5 | <1.0 | 2.5 | 2.5 | 2.5 | 2.5 |
| | pH 8.2 | 5 | 25 | 5 | 10 | 2.5 | 5 | 2.5 | 5 | 5 |
| (G) | pH 6.8 | 75 | 50 | 50 | 50 | 50 | 50 | 50 | 50 | 50 |
| | pH 8.2 | 10 | 10 | 10 | 10 | 5 | 10 | 5 | 5 | 5 |
| (H) | pH 6.8 | >500 | >500 | >500 | >500 | >500 | >500 | >500 | >500 | >500 |
| | pH 8.2 | 500 | 500 | 500 | 500 | 250 | 250 | 250 | 500 | 500 |
| (I) | pH 6.8 | 50 | 50 | 50 | 50 | 50 | 50 | 50 | 50 | 50 |
| | pH 8.2 | 10 | 10 | 10 | 10 | 5 | 10 | 10 | 10 | 10 |
| (J) | pH 6.8 | 25 | 25 | 25 | 25 | 25 | 25 | 25 | 25 | 25 |
| | pH 8.2 | 1 | 5 | 5 | 5 | 5 | 5 | 5 | 5 | 1 |
| (K) | pH 6.8 | 10 | 25 | 10 | 10 | 10 | 10 | 10 | 10 | 10 |
| | pH 8.2 | 1 | 5 | 5 | 5 | 2.5 | 5 | 5 | 5 | 1 |
| (L) | pH 6.8 | 5 | 5 | 5 | 5 | 10 | 5 | 10 | 5 | 10 |
| | pH 8.2 | 1 | 5 | 2.5 | 2.5 | 2.5 | 5 | 2.5 | 2.5 | 1 |

TABLE XV

Minimum Inhibitory Concentrations for Test Compounds in Yeast/Fungi Species (in ppm)

| COMPOUND | An | Ca | Pc | Sc | Tv | Ap | Fo |
|---|---|---|---|---|---|---|---|
| A | 2.5 | 0.50 | 0.25 | 0.50 | 0.25 | 2.5 | 0.50 |
| G | 50 | 50 | 50 | 100 | 100 | 50 | 50 |
| H | 250 | 250 | 100 | 500 | 250 | 250 | 100 |
| I | 50 | 100 | 50 | 100 | 50 | 50 | 100 |
| J | 5 | 10 | 2.5 | 5 | 10 | 5 | 5 |
| K | 1 | 2.5 | 1 | 1 | 5 | 5 | 1 |
| L | 1 | 2.5 | 1 | 2.5 | 2.5 | 1 | 1 |

It has also been discovered that the compounds of the present invention may degrade at a pH of 7 or above over an extended time period to compounds which are less antimicrobially active than the original compounds of the present invention. For example, 3-methylthio-2-propynenitrile is observed to decompose in a basic solution to several compounds, one of which is 3,3-bis(methylthio)propenenitrile, represented below, which is virtually inactive as an antimicrobial.

weight of the appropriately-substituted 2-chloro-3-thio-2-propenenitrile precursor and the like-substituted 3-thio-2-propynenitrile.

A mixture of an appropriately-substituted 2-chloro-3-thio-2-propenenitrile precursor and the like-substituted 3-thio-2-propynenitrile, or a mixture of two or more such appropriately-substituted 2-chloro-3-thio-2-propenenitriles precursors and the like-substituted 3-thio-2-propynenitriles, must be present in an antimicrobial composition in an amount needed to be antimicrobially effective so as to exhibit inhibition of selected organisms. As such, both the appropriately-substituted 2-chloro-3-thio-2-propenenitrile precursor and the like-substituted 3-thio-2-propynenitrile will be present in the mixture in amounts sufficient to make the mixture antimicrobially effective. In essence then, both the appropriately-substituted 2-chloro-3-thio-2-propenenitrile precursor and the like-substituted 3-thio-2-propynenitrile will be present in the mixture in antimicrobially effective amounts. However, because of the benefits of using both the appropriately-substituted 2-chloro-3-thio-2-propenenitrile precursor and the like-substituted 3-thio-2-propynenitrile together, the amounts of each of the appropriately-substituted 2-chloro-3-thio-2-propenenitrile precursor and the like-substituted 3-thio-2-propynenitrile used in the mixture will generally be less than the amount of the appropriately-substituted 2-chloro-3-thio-2-propenenitrile precursor and the like-substituted 3-thio-2-propynenitrile needed when used separately to achieve the same level of both short- and long-term antimicrobial activity as the mixture.

Typically, the amount of such a mixture to be used varies from about 1 part per million (ppm) to about 5,000 ppm by weight. Such amounts vary depending upon the particular mixture tested and organism treated. Also, the exact concentration of the mixtures to be added in the treatment of industrial and consumer formulations may vary within a product type depending upon the components of the formulation. In such formulations, the mixtures of this invention may be added as a liquid concentrate or diluted with additional liquid to produce the ultimate treating composition, wherein the liquid could be water or an organic solvent like glycols, alcohols, acetone and the like.

The increased rate of antimicrobial activity exhibited by mixtures of 2-chloro-3-methylthio-2-propenenitrile and 3-methylthio-2-propynenitrile (Compounds J, K and L) as compared to 2-chloro-3-methylthio-2-propenenitrile alone (Compound G) is demonstrated by the MIC test data shown in Table XIV.

As shown in Table XVI, in a tape joint formulation with a pH between 5 and 7, after 3 months storage at room temperature, the mixtures of 2-chloro-3-methylthio-2-propenenitrile and 3-methylthio-2-propynenitrile (Compounds J and K) protect the tested formulation at a lower level than either the 2-chloro-3-methylthio-2-propenenitrile (Compound G) or the 3-methylthio-2-propynenitrile (Compound A) alone. The composition of the tape joint formulation can be found in Table V.

TABLE XVI

| MEC of Test Compounds in Tape Joint Formulation (in ppm) | |
|---|---|
| Compound | MEC |
| A | >50 ppm |
| G | >50 ppm |
| J | 25-50 ppm |
| K | 25-50 ppm |

As shown in Table XVII, in a paint formulation with a pH between 7 and 9, after 1 month storage at room temperature, the mixtures of 2-chloro-3-methylthio-2-propenenitrile and 3-methylthio-2-propynenitrile (Compounds J and K) protect the tested formulation at a lower level than the 3-methylthio-2-propynenitrile alone (Compound A). The composition of the paint formulation can be found in Table XVIII.

TABLE XVII

| MEC of Test Compounds in a Paint Formulation (in ppm) | |
|---|---|
| Compound | MEC |
| A | >50 ppm |
| J | 25 ppm |
| K | 25 ppm |

TABLE XVIII

| Paint Test Formulation | |
|---|---|
| Raw Material | Percent Weight |
| Hydroxyethyl cellulose | 0.3 |
| Ethylene Glycol | 2.1 |
| Water | 21.7 |
| Acrylic Polymer Dispersing Agent | 0.9 |
| Potassium Tripolyphosphate | 0.1 |
| Octylphenoxypolyethoxyethyl Benzyl Ether Nonionic Surfactant | 0.2 |
| Silicone Defoamer | 0.3 |
| Propylene Glycol | 2.9 |
| Titanium Dioxide | 21.1 |
| Talc | 17.2 |
| Acrylic Latex | 32.1 |
| 2,2,4-Trimethyl-1,3-Pentanediol Monoisobutyrate | 0.9 |
| Ammonium Hydroxide | 0.2 |

What is claimed is:

1. A method for inhibiting microorganisms in a microbial habitat comprising contacting said microbial habitat with an antimicrobially effective amount of a compound corresponding to the formula:

wherein R is an alkyl, cyclic alkyl, aryl, or heterocyclo group selected from the group consisting of thiazolyl, triazolyl, imidazolyl and pyrimidyl.

2. The method of claim 1 wherein R is a straight chain alkyl of 1 to 18 carbon atoms, a branched chain alkyl of 3 to 18 carbon atoms, or a cyclic alkyl of 3 to 8 carbon atoms.

3. The method of claim 2 wherein R is a straight chain alkyl of 1 to 12 carbon atoms.

4. The method of claim 3 wherein R is methyl, ethyl, propyl, butyl, decyl, or dodecyl.

5. The method of claim 2 wherein R is a branched chain alkyl of 3 to 12 carbon atoms.

6. The method of claim 5 wherein R is isopropyl or tertiary butyl.

7. The method of claim 2 wherein R is a cyclic alkyl of 3 to 6 carbon atoms.

8. The method of claim 7 wherein R is cyclopentyl or cyclohexyl.

9. The method of claim 1 wherein R is phenyl, naphthyl, or chlorophenyl.

10. The method of claim 1 wherein the compound is present in an amount from about 1 part per million to about 5,000 parts per million by weight of the compound in the microbial habitat.

11. The method of claim 1 further comprising an antimicrobially effective amount of the appropriately-substituted 2-chloro-3-thio-2-propenenitrile precursor of the compound.

12. The method of claim 11 wherein the compound is 3-methylthio-2-propynenitrile and the appropriately-substituted 2-chloro-3-thio-2-propenenitrile precursor is 2-chloro-3-methylthio-2-propenenitrile.

13. The method of claim 12 wherein the 3-methylthio-2-propynenitrile is present at between about 50 to about 5 weight percent and the 2-chloro-3-methylthio-2-propenenitrile is present between about 50 to about 95 weight percent based on a total weight of the 2-chloro-3-methylthio-2-propenenitrile and the 3-methylthio-2-propynenitrile.

14. The method of claim 13 wherein the 3-methylthio-2-propynenitrile is present at between about 20 to about 10 weight percent and the 2-chloro-3-methylthio-2-propenenitrile is present between about 80 to about 90 weight percent based on a total weight of the 2-chloro-3-methylthio-2-propenentrile and the 3-methylthio-2-propynentrile.

15. The method of claim 11 wherein the compound is present at between about 50 to about 5 weight percent and the appropriately-substituted 2-chloro-3-thio-2-propenenitrile precursor is present between about 50 to about 95 weight percent based on a total weight of the appropriately-substituted 2-chloro-3-thio-2-propenenitrile and the compound.

16. The method of claim 15 wherein the compound is present at between about 20 to about 10 weight percent and the appropriately-substituted 2-chloro-3-thio-2-propenenitrile precursor is present between about 80 to about 90 weight percent based on a total weight of the appropriately-substituted 2-chloro-3-thio-2-propenenitrile and the compound.

17. The composition of claim 11 wherein the appropriately-substituted 2-chloro-3-thio-2-propenenitrile precursor consists essentially of the Z isomer of 2-chloro-3-methylthio-2-propenenitrile.

18. The method of claim 11 wherein the total of the compound and the appropriately-substituted 2-chloro-3-thio-2-propenenitrile precursor is present in an amount from about 1 part per million to about 5,000 parts per million by weight of the compound and the appropriately-substituted 2-chloro-3-thio-2-propenenitrile precursor in the microbial habitat.

* * * * *